United States Patent [19]

Haaga

[11] Patent Number: 4,589,415
[45] Date of Patent: May 20, 1986

[54] METHOD AND SYSTEM FOR FRAGMENTING KIDNEY STONES

[76] Inventor: John R. Haaga, 3409 N. Hilltop, Chagrin Falls, Ohio 44022

[21] Appl. No.: 645,831

[22] Filed: Aug. 31, 1984

[51] Int. Cl.⁴ .............................................. A61B 17/00
[52] U.S. Cl. .................................... 128/328; 128/305; 604/164
[58] Field of Search ............. 128/328, 329, 1 R, 24 A, 128/305, 303 B; 604/164

[56] References Cited

U.S. PATENT DOCUMENTS

| | | | |
|---|---|---|---|
| 3,528,425 | 9/1970 | Banko | 128/329 |
| 3,720,210 | 3/1973 | Diettrich | 604/164 |
| 3,792,701 | 2/1974 | Kloz et al. | 128/7 |
| 3,861,391 | 1/1975 | Antonevich | 128/328 |
| 3,927,675 | 12/1975 | Pohlman | 128/328 |
| 4,027,674 | 6/1977 | Tessler et al. | 128/328 |
| 4,030,505 | 6/1977 | Tessler | 128/328 |
| 4,046,150 | 9/1977 | Schwartz et al. | 128/328 |
| 4,178,935 | 12/1979 | Gekhman et al. | 128/328 |
| 4,196,736 | 4/1980 | Wantanabe | 128/328 |
| 4,203,429 | 5/1980 | Vasilevsky et al. | 128/328 |
| 4,227,532 | 10/1980 | Bluhm et al. | 128/328 |
| 4,311,147 | 1/1982 | Hausler | 128/328 |

Primary Examiner—John J. Wilson
Assistant Examiner—John G. Weiss
Attorney, Agent, or Firm—Body, Vickers & Daniels

[57] ABSTRACT

A method of fragmenting stones that are lodged in a discrete organ of a human body, such as the kidney, which method includes the steps of providing a plurality of elongated tubular sheaths, each formed from a thin walled material with a high acoustical impedance and having an inner passage extending in a given direction from an inlet or first end to an outlet or second end. These tubular sheaths are forced into the body by a trocar adapted to extend through the sheath passage and having a cutting end adapted to extend through the second end of each sheath. As each sheath is forced into the body its position relative to the organ containing the stone is monitored by an appropriate radiographic device so that the end of each sheath is near to, but spaced from, the organ, such as a kidney, with the given direction determined by the elongated passage in each of the sheaths pointing generally toward the stone. After the sheaths have been mounted in the body, each pointing toward the stone but not piercing the organ, an elongated energy transmitting probe is inserted into each of the sheaths for directing acoustical energy through the passages of each of the sheaths and toward the stone; therefore, the energy transmitting probes are energized from, or by, an acoustical power source so that the summation of acoustical energy from the energy transmitting probes at the intersection point in the area of the stone is sufficient to fragment the stone, while the acoustical energy from any one of the probes is generally insufficient to fragment the stone. In this manner, fragmentation of the stone is accomplished with a minimum of tissue trauma.

5 Claims, 10 Drawing Figures

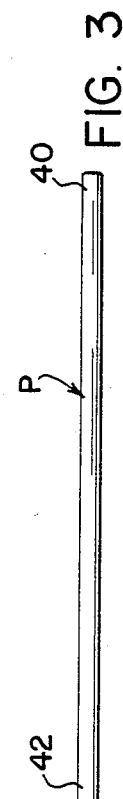
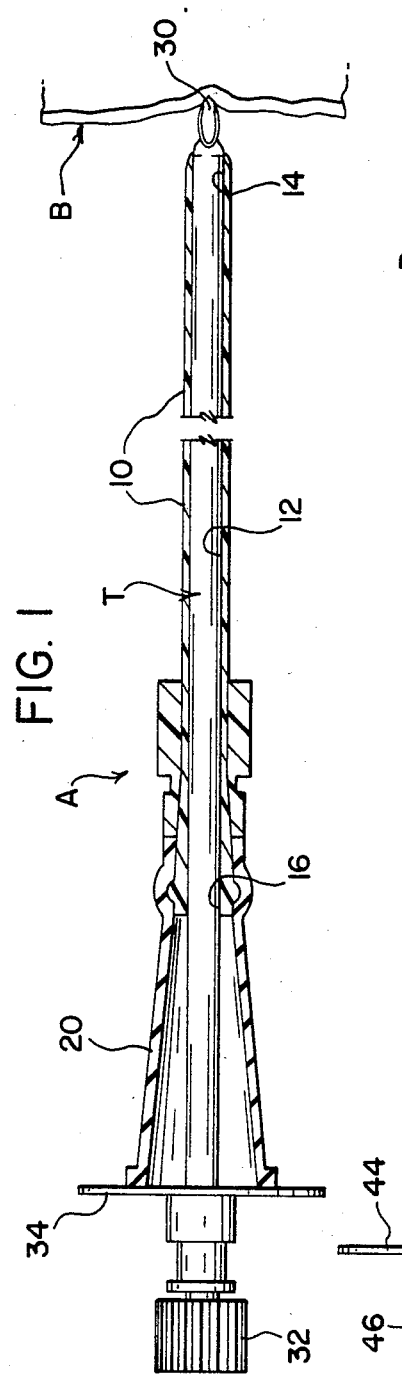
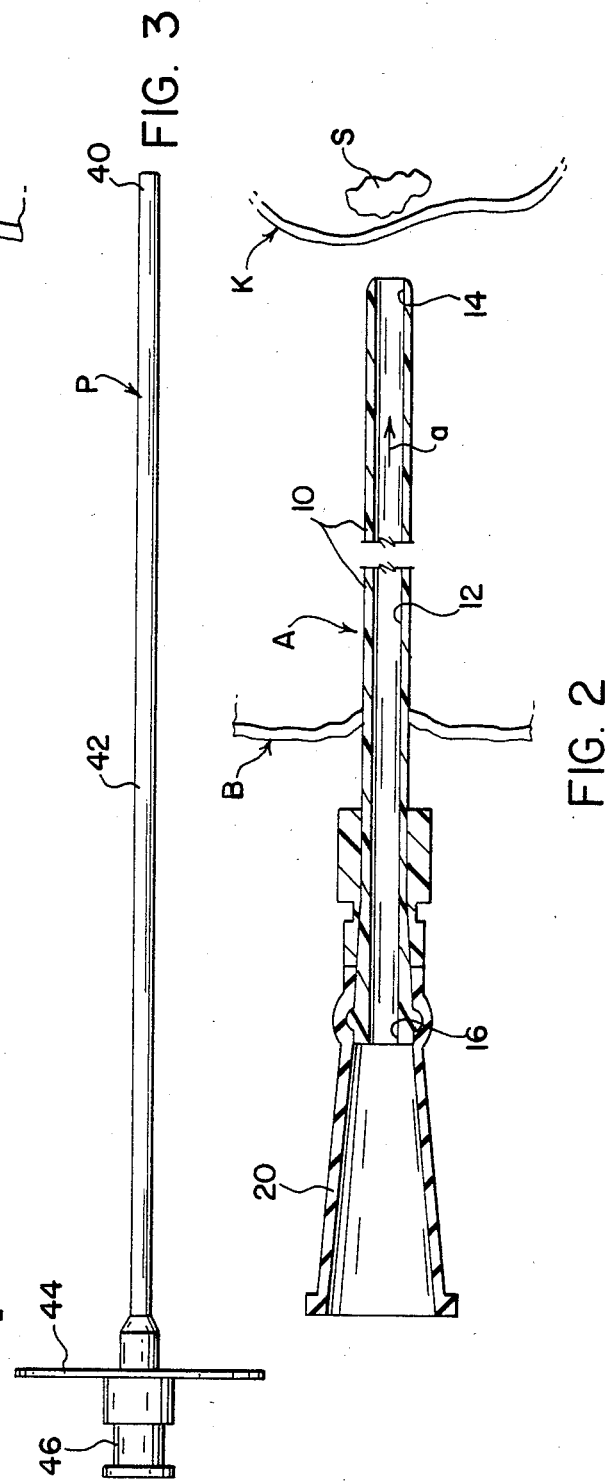

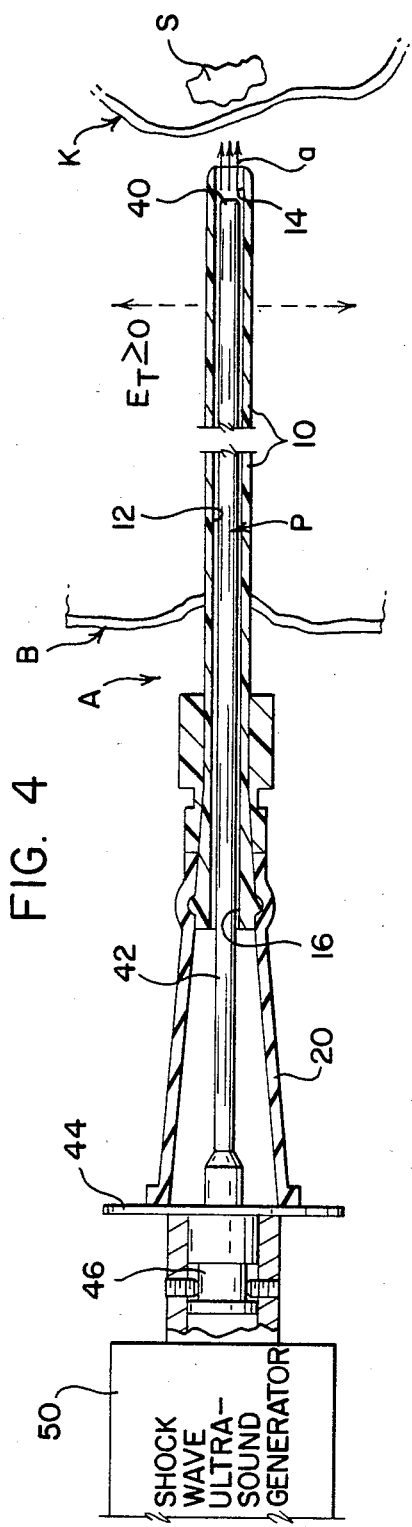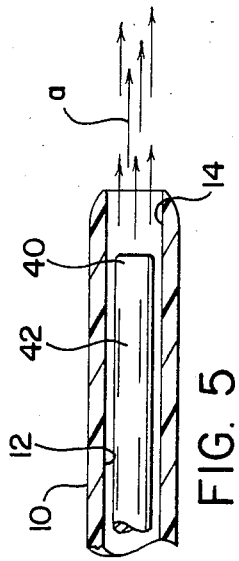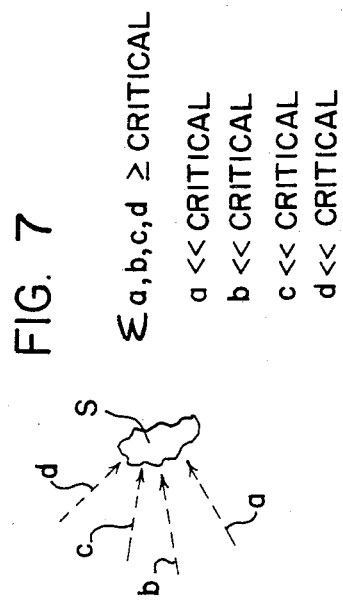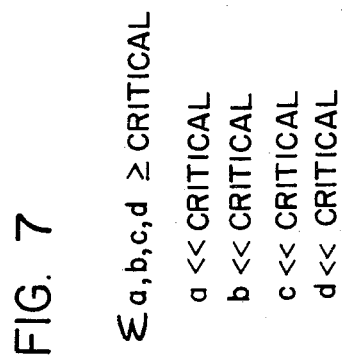

METHOD AND SYSTEM FOR FRAGMENTING KIDNEY STONES

DISCLOSURE

The present invention relates to the art of removing stones from body organs, and more particularly to a method and system of fragmenting a stone lodged in a body organ, such as a kidney.

BACKGROUND OF INVENTION

Nephrolithiasis or stones in a kidney of a human patient is a common condition which can be quite painful and injurious to the kidney if the stone does not pass naturally. Some stones are quite small and begin to flow through the ureter or tube from the kidney to the bladder with natural flow of fluid from the kidney. Although the moving stone can be quite painful, its ultimate passage from the kidney to the bladder does not require any surgical or medical intervention. In other instances, a stone may be small enough to pass into the ureter and become lodged at a position low enough that a mechanical basket or other mechanical manipulator can be passed through the bladder, up the ureter for capturing the stone and mechanically extracting it. When the stone is lodged in the lower portion of the ureter, it is also possible to use catheters and various ultrasonic or vibratory impact devices for disintegrating the stone which can be reached by the catheter. These devices generally involve the use of an ultrasonic transducer as shown in Pohlman U.S. Pat. No. 3,927,675, Antonevich U.S. Pat. No. 3,861,391 and Kloz U.S. Pat. No. 3,792,701. Such impact disintegration devices must engage the stone and transmit disintegration energy to the stone through a transducer of some type located outside the body and connected to the location of the stone through an appropriate catheter extending through the normal urinary tract. These devices generally employ a cystoscope so that the doctor can manipulate the transducer through the catheter and into the appropriate physical relationship with the stone lodged inside the ureter. The transducers must direct enough energy to the stone by a single transducer; therefore, transverse energy losses are high and can cause some trauma. The time for disintegration can be long due to the inability of transmitting high energy. Other similar devices have been suggested for disintegrating stones by passage of a catheter and instruments through the bladder into the position adjacent the stone causing the physical difficulty. An electric discharge device is shown in Tessler U.S. Pat. No. 4,027,674. An explosive device is shown in Watanabe U.S. Pat. No. 4,196,736. A combined ultrasonic and physical grapling device is illustrated in Schwartz U.S. Pat. No. 4,046,150. All of these patents are incorporated by reference herein for the purpose of background information.

The devices and systems described above and shown in the prior art patents using cystoscopes, catheters and various mechanical devices can not be used for the situation when the stone occurs in the upper portion of the kidney and is too large to pass through the outlet tube or ureter into the bladder or into the lower portion of the ureter where it can be reached from outside the body. The existence of a stone lodged in the kidney which can not, or does not, pass from the kidney can cause blockage and requires removal, sometimes on an emergency basis. In the past, the only system or method generally used for removing such stones lodged in the kidney was a surgical procedure wherein the patient was generally anesthesized and an incision was made through the body and into the kidney itself by surgical instruments so that the stone could be visually exposed and manually removed with appropriate instruments. This surgical procedure required a substantial amount of recuperation primarily because of the trauma resulting from the large incision required to reach the remote body area where the kidney is located. An incision in the kidney or the outlet of the kidney and through the heavy muscular portion of the patient required a substantial recuperation time, lengthy discomfort and the normal risk involved in any major surgery.

In recent years two medical developments have been made to simplify the removal of a stone lodged in the kidney, or other body organ, when the stone causes infection, blockage or other serious situation and is too large to pass simultaneously from the organ through the normal body passages. The first system is percutaneous nephrotomy combined with dilation of the surgical passage into the kidney and removal of the stone or renal calculus from the kidney. The second is generally referred to as extracoporeal ultrasonic lithotripsy. Both of these new procedures have evolved from normal advances in surgical and ultrasonic technology; however, they are not completely acceptable because of certain problems experienced with their use.

The percutaneous nephrotomy and dilation method involves the use of a radiographic device, such as a fluoroscope, ultrasonic screen or CT, which device shows the kidney stone within the kidney so that a needle from outside the body can be forced directly into the collecting system or central cavity of the kidney itself. Following this actual renal puncture, an angiographic wire having a plastic catheter is forced into the kidney. This procedure of a catheter with a wire being directed into the kidney from outside the body is usually performed with local anesthesia; however, it could involve general anesthesia which presents some normal patient difficulty. After a needle has been passed into the kidney and a wire with a plastic catheter is forced through the opening to the kidney, the patient is then placed under a general anesthesia so that progressively larger sizes of catheters can be positioned over the wire extending from outside the patient to inside the kidney. Progressive increasing of the size of the catheters dilates the passageway from the skin to the kidney itself until a large plastic sheath measuring 28–30 French is left in place to provide a passage from outside the patient to the kidney. After this large plastic sheath is positioned by the angiographic wire, the stone in the kidney can be removed manually by instruments such as a wire basket employed in the past for removing stones through the urinary tract. In some instances, a grinding device is used to reduce the size of the stone until it can be removed manually through the plastic sheath remaining in the body. This method is surgical in nature; however, it is preferred over the standard surgical approach because the percutaneous procedure is less injurious to the kidney and less traumatic to the patient. Consequently, the recovery time and discomfort is greatly reduced. Even though this particular medical procedure for removing stones lodged in the kidney is quite an improvement over general surgery, there is some difficulty in that the kidney is punctured. Other organs adjacent the kidney may be inadvertently punctured. Also, the kidney can be ruptured to cause hemorrage or severe trauma to the kidney and to the various organs around the kidney, such as the liver or spleen. These disadvantages are outweighed by the advantages over general surgery in certain instances and this method is employed as generally accepted practice for removing kidney stones.

Referring now to the extracoporeal ultrasonic lithotripsy procedure, the kidney stone lodged in the kidney is eliminated without incisions or catheter penetration of the urinary tract. In this system, a biplane x-ray machine localizes the renal calculi in a particular patient. The patient is then placed in a very large water bath so that the whole body, except the head and neck, is immersed in the water. The patent is then anesthetized, either with a general or spinal anesthesia, and the x-ray machine is used to focus hydraulic shock waves onto the stone within the kidney. After this focusing process, high intensity shock waves are generated in the water bath and these waves are transmitted through the water to the stone within the kidney. This shock wave is applied for a long time, as long as 30 or 40 minutes, which causes disintegration of the stone into relatively small granular pieces that can be passed naturally through the ureter into the bladder and from the bladder in normal bladder function. This medical procedure has become widely publicized and is sought by many patients; however, it involves a device that is very expensive to obtain and extremely expensive to maintain. Each machine will last for a very short time, in the neighborhood of five to six years so that the high cost of the machine must be amortized over a relatively short period. In view of the expense, only a few hospitals can justify purchasing and maintaining this type of a device. Beyond the cost factor, these devices, which are now coming into use, have been found to present some difficulty in attempting to focus the sound wave onto a very small stone located in the inside of the patient. Such a focusing problem requires substantial skill. If the sound waves are not properly focused, the kidney itself and adjacent tissue can be agitated with the resulting trauma. Also, these devices use traditional x-ray machines with the normal radiation concerns and the inability to detect certain stones, such as uric acid stones.

As can be seen, tremendous medical advance has been realized in the area of management of kidney stones for convenient and safe removal. Even with these advances, the latest medical technology has certain disadvantages, such as cost and possible tissue trauma, which bode against universal use of the newly developed techniques.

THE INVENTION

The disadvantages of general surgical removal of kidney stones and of the two recent developments in this area are overcome by the present invention which relates to a method and system for fragmenting a stone in an organ, such as a kidney, which is relatively inexpensive, involves little tissue trauma and is easily used by persons with a minimum amount of normal medical training.

In accordance with the new system and method, a number of individual probes are introduced through the skin to a location directly adjacent the organ containing the calculi, such as the kidney for a kidney stone. Although a kidney stone will be discussed as the preferred embodiment, it is appreciated that other organs, such as gall bladders or bile ducts, may have stones which can be treated in accordance with the present invention. Consequently, the description with respect to the kidney stones applies generally to other stones contained in discrete organs of the human body. The probes are made specifically for introduction into the patient through the skin. After they are properly positioned, beams of ultrasonic energy or shock waves are transmitted to the stone from the probes located outside the organ. This focusing of several ultrasonic energy beams or shock waves onto the renal calculi will fragment the calculi into particles sufficiently small to pass simultaneously from the ureter and through the normal urinary tract. This procedure avoids the disadvantages of the other two more recently developed processes and methods for medically removing lodged stones from kidneys. Once the stone or calculus has been located under some type of radiographic device, such as a fluoroscope, ultrasound or CT, the location of the stone, kidney and the probes are monitored as the probes are being forced into the patient to positions wherein the probes are spaced from the organs and are pointed toward the stone within the organ or kidney to be fragmented. Since substantially continuous monitoring of the relative positions of the probes and the stone together with the organ is used, the CT is preferred as the best modality to be employed. This provides superior spatial and contrast resolution of the body cavity in which the probes are mounted to show various organs and also various types of stones, including the difficult to detect uric acid stones. Since the CT is capable of visualizing uric acid stones due to its known contrast resolution characteristics, this preferred arrangement is employed for monitoring the insertion of the various probes so that they do not enter the kidney or the organ, but are placed as close as possible to the stone while remaining outside the organ. More than one probe, indeed several probes in some cases, are employed in practicing the system and method in accordance with the present invention. In this manner, sufficient energy can be delivered to the stone or calculus so that it will be fragmented or disintegrated into small pieces in a relatively short period of time. This process has a distinct advantage over previous systems in that there is no direct puncture or incision into the kidney itself.

After a CT scan illuminates the kidney in the abdominal cavity of a patent the kidney stone will be visible; therefore, the first probe is forced into the body to a position adjacent the kidney and pointing toward the stone. This probe includes an outer plastic sheath having an inner opening facing toward the stone or calculus to be destroyed after the sheath has been forced into the body by a standard trocar. The trocar itself does not enter the kidney, so the sheath is away from the kidney a distance that accommodates the point of the trocar during the insertion process. After a plurality of sheaths are forced into the body, a metal transmitting probe is placed into each of the plastic sheaths with a transmitting head facing toward the stone. These probes will transmit beams of ultrasonic energy or shock waves through the metal probes, out the plastic sheaths and toward the calculus within the kidney. Each sheath or metal probe thus creates a beam of acoustical energy that is tramsmitted to the kidney stone and is focused on the stone so that it fragments and passes through the normal collecting system of the kidney and through the urinary tract. The radiographic monitoring continues to assess the status of the stone so that the energy and frequency of the energy carrying beam may be adjusted to assure rapid disintegration or fragmentation of the calculus or stone.

This method and system has several advantages over the three generally used systems for removing a kidney stone lodged in the kidney or the upper portion of the ureter. There is only minimal injury to body tissue by forcing the probes or sheaths into the body as relatively small rod like devices. No major surgical incision is made in the body, nor is the kidney itself punctured. Consequently, when compared with the normal general surgical method of stone removal, recuperation time will be relatively short. Also the expense of performing the new method will be much less than the cost of a general surgery. In view of the fact that no incision is made in the kidney, normal risk of infection and other damage to the kidney and related organs is reduced if not actually eliminated. As can be seen, the present invention is a marked improvement over, and overcomes the disadvantages of, the general surgical stone removal procedure.

With respect to the prior percutaneous method where catheters are inserted into the kidney and dilated for mechanical removal of the stone, the present method and system has several advantages. There is a reduction in the trauma or injury to the patient during the procedure. Recuperation time is less since the diameter of the plastic probes employed in accordance with the present invention is only large enough to allow insertion of a wire-like energy transmitting probe. The plastic sheaths or probes are not expanded as in the previous catheter and dilation procedure. Thus, only superficial injury to the body itself is realized. There is a lesser muscle damage. The kidney itself is not punctured, as in the previous catheter and dilation system. Consequently, the present invention removes any major complications which can result from damage to the kidney or adjacent organs by the normal penetration and manipulation of the kidney as previously envisioned by the catheter and dilation and manipulation system. In addition, by using the preferred CT scan system for monitoring the location of both the organ and the stone together with the actual position of the probes used to disintegrate the stone, more accurate focusing of the energy in the body results. Also uric acid stones can be identified, located and removed.

When comparing the present system to the extracoporeal lithotripser, several advantages are realized. First, the present invention relates to a system and method which is substantially less expensive to build and maintain. It will, thus, be affordable by most, if not all hospitals, and available to all patients. The complicated lithotripsy sound wave or acoustical wave transmitting system for generating and delivering the energy to the stone is replaced by a simple procedure. As another advantage over lithotripsy, the present invention provides far superior concentration of energy in the stone itself by providing several acoustical sources generated at, or near, the organ itself together with the intersection of various energy beams at the stone itself by relatively easily learned monitoring techniques. Using a CT scan for guiding the various probes into the proper position with respect to the kidney, there is extremely close control of the actual energy used, since the CT can monitor the disintegration of the stone. By accurate focusing of several energy beams onto the stone, while watching the stone, there is less likelihood of vibrational damage to surrounding tissue, including the tissue of the kidney. The improved ability to focus the energy from several beams directly onto the stone by relatively simple manipulations drastically reduces the necessity for higher energy and any propensity for trauma to adjacent tissue. By using many beams exposed only from a location adjacent the kidney, stray energy absorption by the body is minimized.

Another advantage of the accurate focusing and precise energy delivery characteristics of the present invention is that this invention can be used in conjunction with a more general energy delivery system. Thus, the present probe arrangement may be useful to augment a general delivery system, such as used in an extracoporeal lithotripser. Consequently, the combination of the present invention, together with previous devices for delivery of energy to disintegrate a kidney stone, is within the contemplation of the present invention. For instance, it may be possible to use one or more of the probes used in this invention with a catheter and disintegrator in the urinary tract.

One basic advantage of the present invention is the ability to deliver the critical amount of acoustical energy at the stone itself. Since the focusing probes employed in the present invention could be used in combination with other energy delivery systems, the present invention has general applicability and could be used with a single probe in some instances. This feature is also contemplated by the present invention even though it is generally intended that more than one probe is inserted into the body cavity to a location near to, but not penetrating the organ. By using a number of probes to deliver the energy, sufficient destructive energy can be focused and absorbed by the calculus due to intersecting energy beams from the various probes. The energy beam from each of the probes is not sufficient to cause damage to the tissue or to disintegrate the calculus. Only when the energy from a plurality of the probes is combined at the intersection or focus point of the beams on the stone, is the energy sufficient to disintegrate the stone. To assure that the destructive energy does not combine in the adjacent tissue surrounding the various probes, it is essential that the sheaths defining the probes be formed from a material having a relatively high acoustical impedance. In this manner, the energy transmitted through the sheaths by the transmitting probes will pass in a direction generally intersecting the kidney stone without dissipation to, and heating of, adjacent body tissue. This focusing of the energy beams can be modified by changing the construction of the wire-like metal transmitting probes or transducers extending through the sheaths toward the stone in the kidney. The beams can be made to converge or diverge slightly to match the desired characteristics of a particular stone being disintegrated or fragmented. A number of probes used to obtain the critical energy for disintegration of the stone or calculus is adjusted and determined in each patient.

In accordance with the present invention there is provided a method for fragmenting a stone, as defined above, when the stone is lodged in a discrete organ of a human body. The method comprises the steps of providing a plurality of elongated tubular sheaths, each formed from a thin walled material with a high acoustical impedance and having an inner passage extending in a given direction from the inlet end of the sheath to the outlet end of the sheath. These elongated sheaths have a relatively small diameter and are forced into the patient by a trocar extending through the central passage of the sheath and from the outlet end of the sheath to allow insertion and guidance of the sheath into the body to a position with each of the sheaths having its outlet end near to, but spaced from, the organ or kidney so that the passage of each of the sheaths points directly toward the stone. The trocar is removed after a sheath is positioned. The same trocar may be used to force the next sheath into the proper position with the central passage pointing toward the stone in the kidney. After the desired number of probes have been located with the central passages pointing toward the stone, elongated energy transmitting probes are inserted into each of the sheaths for directing acoustical energy through the passages of the sheaths. The transmitting probes are then energized by independent or combined external acoustical power supplies or sources. The summation of the acoustical energy at the stone itself is sufficient to fragment the stone while the acoustical energy from any one of the various sheaths is generally insufficient to fragment the stone. In accordance with another aspect of the invention, the forcing of the sheaths into the body is monitored by an appropriate radiographic device. This device, preferably, is a CAT scan to display the organ and the stone lodged therein.

The primary object of the present invention is the provision of a system and method of fragmenting a stone lodged in an organ of a human body, which method and system are relatively inexpensive, involve a minimum of adjacent tissue trauma, can be used with a minimum of training and are relatively safe for general use.

Still a further object of the present invention is the provision of a system and method, as defined above, which system and method involve directing energy beams from outside the body to a location adjacent the organ and then focusing the beams on the stone without penetrating or puncturing the organ.

These and other objects and advantages will become apparent from the description of the preferred embodiment of the invention as shown in the accompanying drawings described below.

BRIEF DESCRIPTION OF DRAWINGS

FIG. 1 is a partially cross-sectioned side view illustrating a single probe of the present invention with a trocar inserted therein preparatory to entering the body of a patient;

FIG. 2 is a cross-sectional side view of the probe shown in FIG. 1, in the proper position within the body of a patient with the inserted trocar removed;

FIG. 3 is a side elevational view of an acoustical energy transmitting probe employed in the preferred embodiment of the present invention;

FIG. 4 is a cross-sectional side view, similar to FIG. 2, employing the probe of FIG. 3 and illustrating, schematically, a shock wave or ultrasound generator for transmitting energy through the probe shown in FIG. 3;

FIGS. 5 and 6 are partial, enlarged cross-sectional views illustrating two separate types of transmitting probes;

FIG. 7 is a schematic diagram illustrating the relationship of the energy beams focused on a stone to be fragmented; and, FIGS. 8, 9 and 10 show procedural steps employing the system and method of the present invention.

PREFERRED EMBODIMENT

Figure 8:
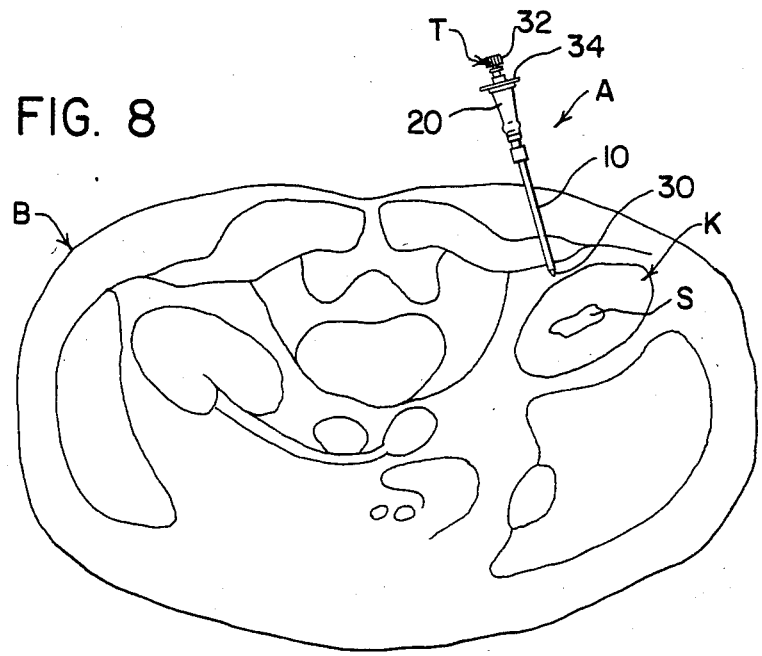

Referring now to the drawings wherein the showings are for the purpose of illustrating the preferred embodiment of the invention only and not for the purpose of limiting same, FIG. 1 shows probe A in the form of an elongated sheath 10 having a relatively thin outer wall formed from a plastic material having a relatively high acoustical impedance and including elongated inner passage 12 with an outlet end or opening 14 and inlet end or opening 16. An appropriate inlet nipple 20 formed from another plastic material is secured over the end 16 of sheath 10. Sheath 10 is rigid and selfsustained whereas the nipple 20 can be somewhat pliable and flexible for easy access to opening 16. Sheath 10 is adapted to be forced into a patient's body B into a position adjacent a kidney K for the purpose of fragmenting kidney stone S into relatively small particles for normal passage through the urinary tract. To facilitate insertion of probe A, an appropriate trocar T is inserted in passage 12. The trocar includes an outwardly facing cutting end 30, which end extends beyond outlet end or opening 14 of sheath 10 for the purpose of forming a cut in the tissue of the body to allow inward movement of probe A after the patient has been appropriately anesthesized. Handle 32 of trocar T is manipulated to guide sheath 10 into the proper position as basically shown in FIG. 2 wherein the outlet end 14 is near to, but spaced from kidney K. A thrust plate 34 can be used for thrusting the trocar into the proper position to leave the sheath 10 forming probe A in the desired position. Of course, the trocar cutting end 30 does not extend beyond outlet end 14 a distance which would penetrate the kidney during the inward forcing action. The kidney stone and other vital organs of the body B are monitored by appropriate radiographic device, such as a CT or CAT scan to properly position the sheath 10, as shown in FIG. 2 with the passage 12 defining the direction a, which is illustrated as an energy beam a in the remaining figures. After the probe A is mounted as shown in FIG. 2, an appropriate wire-like metal energy transmitting probe P, shown in FIG. 3, is inserted into probe A. The transmitting probe includes an innermost end 40 for directing beams of ultrasonic energy or sound waves along shaft 42 of the probe P. An appropriate mounting plate 44 and coupling 46 are employed for the purpose of connecting the metal probe P onto an appropriate shock wave or ultrasonic sound generator 50, which device is well known in the art. Many types of these devices can be used for the purpose of transmitting a sound wave along shaft 42 to end 40 of the transmitting probe P. This creates an energy beam a from a position outside kidney K and directs the beam to the stone S within the kidney for the purpose of disintegrating the stone. The energy of beam a is insufficient for disintegration. This low energy level of beam a, combined with the high acoustical impedance of sheath 10, prevents the transverse energy $E_T$ from being of a significant magnitude to cause trauma in adjacent tissue. This low or negligible transverse energy is illustrated by the dashed arrows in FIG. 4. Energy beam a directed from end 50 of probe P is schematically illustrated in FIG. 5 as having a direction defined by passage 12 and extending from inside sheath 10 to the stone. In some instances, it may be desirable to cause the beam to be dispersed or otherwise controlled. This is schematically illustrated in FIG. 6 as beam a' extending from end 40' of a modified probe.

Although it is possible that a single probe A could be used in conjunction with other energy directing systems, in the preferred embodiment of the present invention and generally in accordance with the present invention, more than one probe is located in the body and directed toward stone S. In this manner, the energy beam from more than one probe will intersect the stone and cause sufficient concentration of a critical energy necessary for fragmentation of the stone within reasonable length of time. The frequency and intensity of beam a will be controlled according to the composition and size of the stone and the physical characteristic of the stone encountered during fragmentation. As shown in FIG. 7, more probes A are emloyed, each having a beam a, b, c, and d, which beams are summed at stone S for the purpose of exceeding the critical fragmentation energy of the stone. As illustrated in this figure, each of the beams has an energy substantially less than the critical energy so as to preclude adjacent tissue trauma by the beams from the various probes. In this manner, only the stone itself is exposed to a high level of acoustical energy. This is a different concept than the extracoporeal lithotripser wherein energy concentration may be in the general area of the stone, but not precisely located, as when using the present invention.

Figure 9:
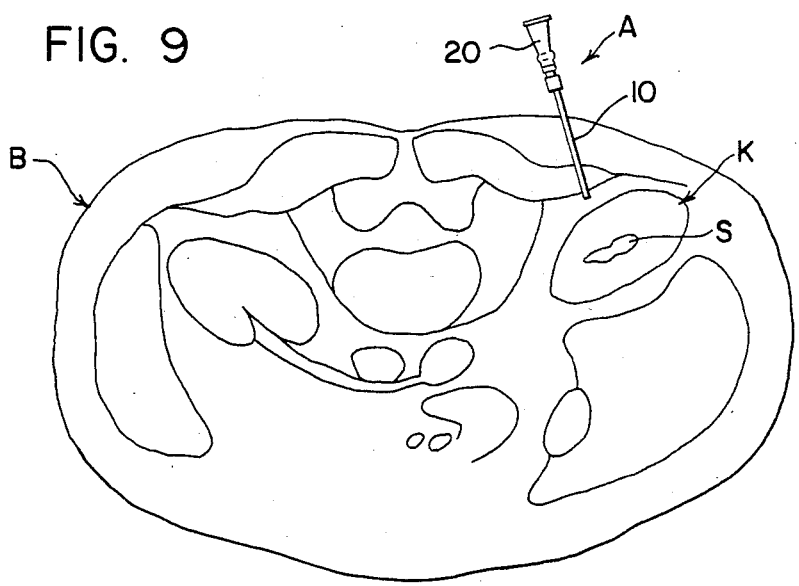
Figure 10:
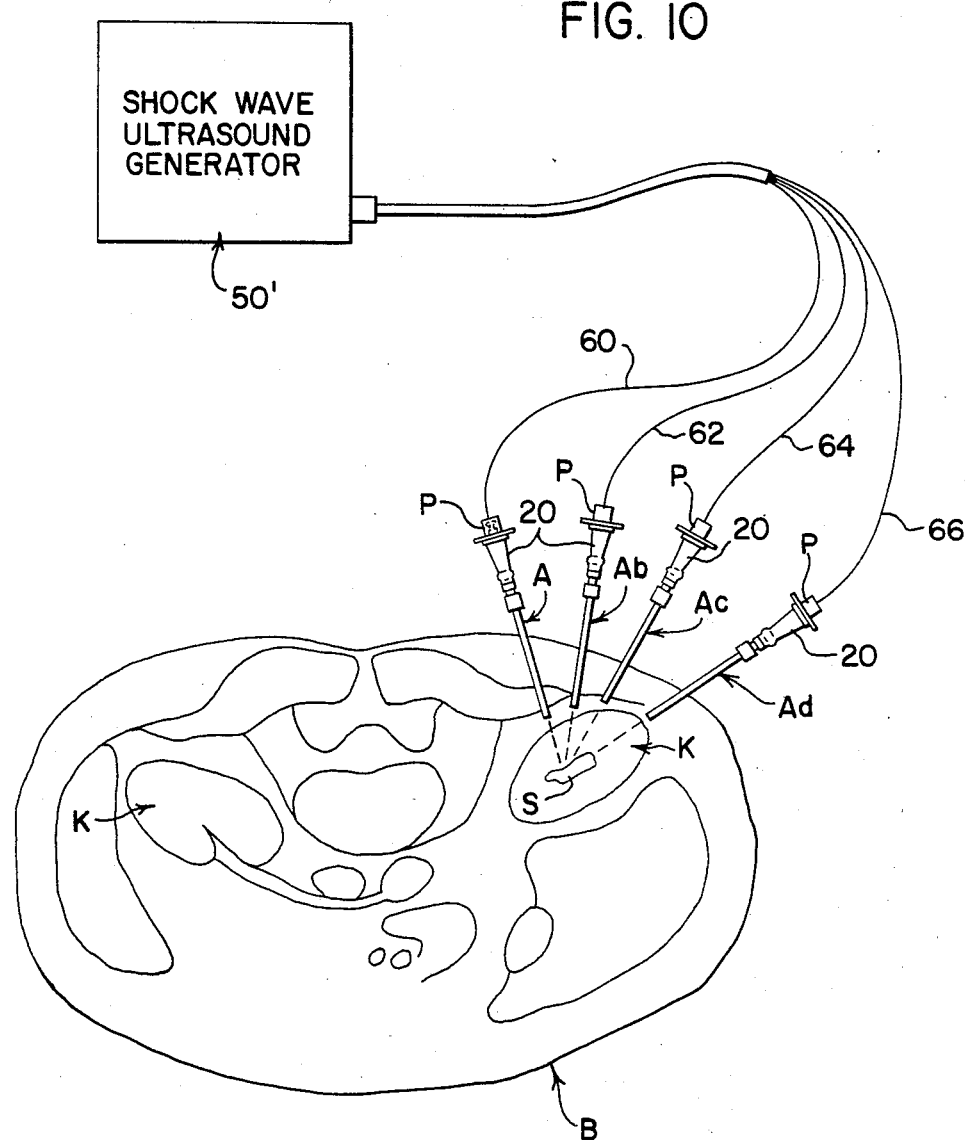

The general implementation of the system and method of the present invention is illustrated progressively in FIGS. 8, 9 and 10. The trocar T is used for inserting probe A into the position shown in FIG. 8. As the probe is forced into this position, the total body cavity shown in FIG. 8 is visualized by a CAT scan or other appropriate radiographic device. After the proper location of probe A is realized with the end of the probe outside of kidney K, trocar T is removed. Then several other probes A are inserted. This is shown in FIG. 10 wherein probe A and additional probes Ab, Ac, and Ad are assembled in the same fashion. Each of these probes has an end outside kidney K and is used to direct acoustical energy along a beam directed to stone S. An appropriate shock wave or ultrasound generator 50' is employed wherein transducer leads 60, 62, 64 and 66 are coupled with the ends of each of a single probe P mounted within the various probes A, Ab, Ac, and Ad. These various probes P, when energized by the generator or power supply 50' create the energy beams shown in FIG. 7 for the purposes of disintegrating stone S. The progress of the disintegration can be observed by an appropriate radiographic device such as a CT device.

The length, diameter and composition of the sheath 10 may be selected in a variety of combinations to produce a high acoustical impedance and allow introduction into the appropriate position by a trocar. An energy transmitting probe P will also have an appropriate diameter, configuration and material selected in accordance with the desired wave length and amount of energy to be transmitted through the probe A into the stone S. The tip of the probe remains within the sheath 10 so that the sheath will guide the energy beam to control its focusing action against the stone.

Having thus described the invention, it is claimed:

1. A method of fragmenting a stone lodged in a discrete organ of a human body, said method comprising the steps of:
   (a) providing a plurality of elongated tubular sheaths, each formed from a thin walled material with a high acoustical impedance and having an inner passage extending in a given direction from an inlet first end to an outlet second end;
   (b) forcing said sheaths into said body by a trocar extending through said passage and from said outlet second end to positions of said sheaths wherein said outlet second end of said sheaths is near to, but spaced from, said organ and said given direction of the passage in each of said sheaths points generally toward said stone;
   (c) removing said trocar;
   (d) inserting an elongated energy transmitting probe into each of said body mounted sheaths for directing acoustical energy through the passages and toward said stone when said transmitting probes are each energized by an acoustical power source; and,
   (e) energizing each of said transmitting probes individually with an acoustical power source with the summation of acoustical energy from said sheaths and at said stone being sufficient to fragment said stone while the acoustical energy from any one of said sheaths being generally insufficient to fragment said stone.

2. A method as defined in claim 1 including the further step of monitoring said forcing step by a radiographic device.

3. A method as defined in claim 2 wherein said radiographic device is a CAT scan providing a display of said organ and of said stone lodged therein.

4. A method as defined in claim 1 wherein said organ is a kidney.

5. A system for fragmenting a stone lodged in a discrete organ of a human body, comprising:
   (a) a plurality of elongated tubular sheaths, each formed from a thin walled material with a high acoustical impedance and having an inner passage extending in a given direction from an inlet first end to an outlet second end:
   (b) means for forcing said sheaths into said body to positions wherein said outlet second end of each of said sheaths is near to but spaced from, said organ and said given direction of the passage in each of said sheaths points generally toward said stone, said forcing means including a removable trocar extending through said passage and from said outlet end;
   (c) an elongated energy transmitting probe adapted to fit into each of said body mounted sheaths for directing acoustical energy through the passages and toward said stone when said transmitting probes are each energized by an acoustical power source; and,
   (d) means for energizing each of said transmitting probes with a separate acoustical energy from said sheaths and at said stone being sufficient to fragment said stone while the acoustical energy from any one of said sheaths being generally insufficient to fragment said stone.

* * * * *